United States Patent [19]

Meister et al.

[11] Patent Number: 4,758,551

[45] Date of Patent: Jul. 19, 1988

[54] METHODS FOR COMBATTING RENAL TOXICITY DUE TO METALS OR NEPHROTOXIC DRUGS AND FOR SELECTIVELY MODULATING IN VIVO FORMATION OF LEUKOTRIENE TYPES

[75] Inventors: Alton Meister; Mary E. Anderson, both of New York, N.Y.

[73] Assignee: Cornell Research Foundation, Inc., Ithaca, N.Y.

[21] Appl. No.: 883,400

[22] Filed: Jul. 8, 1986

[51] Int. Cl.$^4$ ............................................. A61K 37/02
[52] U.S. Cl. ..................................................... 514/18
[58] Field of Search .................................... 514/18, 19

[56] References Cited

PUBLICATIONS

Methods of Enzymol., 113:555–564, (1984).
J. Chem. Soc., pp. 1959–1963, (1950).
J. Chem. Soc., pp. 886–894, (1957).
J. Biol. Chem., 248:2836–2844, (1973).
J. Amer. Chem. Soc., 75:4607–4608, (1953).

*Primary Examiner*—Delbert R. Phillips
*Attorney, Agent, or Firm*—Sughrue, Mion, Zinn, Macpeak, and Seas

[57] ABSTRACT

The present invention relates to a method for combatting renal toxicity due to metals or nephrotoxic drugs. More specifically, the present invention relates to the administration of gamma-glutamyl amino acids to a subject so as to combat renal toxicity due to metals or nephrotoxic drugs. The present invention also relates to a method for selectively modulating in vivo formation of leukotriene types comprising administering gamma-glutamyl amino acids to a subject.

6 Claims, 1 Drawing Sheet

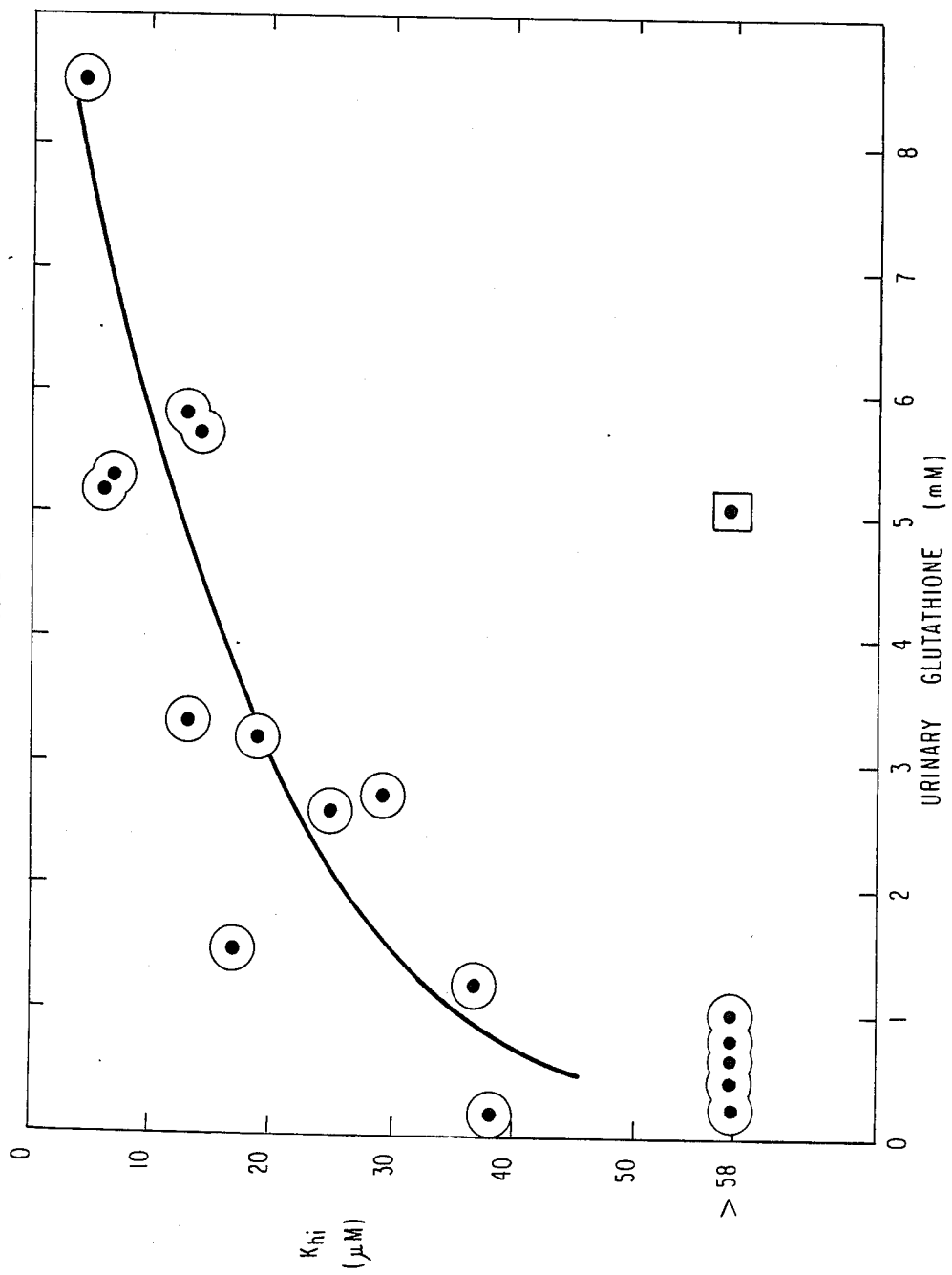
FIGURE

METHODS FOR COMBATTING RENAL TOXICITY DUE TO METALS OR NEPHROTOXIC DRUGS AND FOR SELECTIVELY MODULATING IN VIVO FORMATION OF LEUKOTRIENE TYPES

This invention was made with Government support under National Institutes of Health Grant AM-12034 and American Cancer Society Grant BC850. The Government has certain rights in this invention.

FIELD OF THE INVENTION

The present invention relates to a method for combatting renal toxicity due to metals or nephrotoxic drugs. More specifically, the present invention relates to the administration of gammaglutamyl amino acids to a subject so as to combat renal toxicity due to metals or nephrotoxic drugs. The present invention also relates to a method for selectively modulating in vivo formation of leukotriene types comprising administering gamma-glutamyl amino acids to a subject.

BACKGROUND OF THE INVENTION

Recent studies on the metabolism of glutathione indicate that glutathione is exported from many types of cells (see Meister, A. et al, *Ann. Rev. Biochem.* 52:711–760 (1983) and Larssen, A. et al, Ed., Functions of Glutathione - Biochemical, Physiological and Toxicological Aspects, Raven Press, New York (1983)). Glutathione exported from the liver accounts for most of the blood plasma level of glutathione, a large fraction of which is utilized by the kidney. However, this pathway of inter-organ transport of glutathione accounts for only some of the glutathione which is exported from cells. That is, export of glutathione from the kidneys into the blood and bile is several times greater than that from the liver. Such exported glutathione is utilized within the kidney tubule by the action of gamma-glutamyl transpeptidase and dipeptidase. Gamma-glutamyl transpeptidase characterizes the first step in the degradation of glutathione.

It has been shown that administration of certain inhibitors of gamma-glutamyl transpeptidase such as L-(or D-) gamma-glutamyl-(o-carboxy)phenylhydrazide, other hydrazides, 6-diazo-5-oxo-L-norleucine and L-(α S, 5S)-α-amino-3-chloro-4,5-dihydro-5-isoxazole acetic acid (hereinafter "AT-125") leads to substantial urinary excretion of glutathione (see Griffith, O. W. et al, *Proc. Natl. Acad. Sci.*, USA, 76:268–272 (1979) and Griffith, O. W. et al, *Proc. Natl. Acad. Sci.*, USA, 76:5606–5610 (1979)).

Although the isomers of gamma-glutamyl-(o-carboxy)phenylhydrazide are good inhibitors for gamma-glutamyl transpeptidase, they are split to a slight extent by gamma-glutamyl transpeptidase. This leads to the formation of o-carboxyphenylhydrazine, which is toxic and doses of more than 2 mM per kilogram of body weight have been found to be fatal in mice. Further, although AT-125 is a potent gamma-glutamyl transpeptidase inhibitor, it also inhibits a number of other enzymes, for example, glutamine amidotransferases (see Hanka, L. J. et al, *Cancer Chemo. Rep.* 57:141–148 (1973) and Neil, G. L. et al, *Cancer Res.* 39:852 (1979)).

Glutathione reacts with various endogenous and exogenous (including toxic compounds) to form S-substituted glutathione conjugates. These conjugates are usually metabolized. The first step of such metabolism is the cleavage of the gamma-glutamyl group from the glutathione conjugate by gamma-glutamyl transpeptidase. For example, methylchloride forms a conjugate with glutathione and metabolism of the resulting glutathione conjugate leads to formation of a toxic product, though to be $H_2S$. Inhibition of gamma-glutamyl transpeptidase by AT-125 inhibits conversion of the glutathione conjugate to the toxic product and thus decreases the toxicity of methyl chloride in mice (see White, R. D. et al, *Pharm.* 24:172 (1982)). However, since AT-125 is highly toxic and a non-specific inhibitor of gamma-glutamyl transpeptidase it can not be advantageously employed.

Moreover, methyl mercury forms a complex with glutathione and is excreted in this form in the urine. Excretion of this toxic compound as a glutathione complex is greatly increased after administration of AT-125 (see Gregus, Z. et al, *The Toxicologist* 6:150 (1986)). Again, since AT-125 is highly toxic and a non-specific inhibitor of gamma-glutamyl transpeptidase it can not be advantageously employed.

In addition, selenium poisoning is accompanied by incorporation of selenium in place of sulfur in glutathione. Heretofore, bromobenzene has been given to selenium-intoxicated animals on the premise that this would stimulate the urinary excretion of the selenium analog of glutathione. However, the use of bromobenzene is disadvantageous because, like AT-125, it is highly toxic and a non-specific inhibitor of gamma-glutamyl transpeptidase (see Moxon, A. L. et al, *J. Biol. Chem.* 132:785–786 (1940), Lemley, R. E., *J. Lancet* 60:258 (1940) and Westfall, B. B. et al, *J. Pharmacol.* 72:245–251 (1941)).

As discussed above, AT-125 and other inhibitors of gamma-glutamyl transpeptidase are toxic and non-specific inhibitors. Thus, these inhibitors are disadvantageous for combatting renal toxicity.

It has been found that gamma-glutamyl amino acids inhibit, in vivo, gamma-glutamyl transpeptidase and the administration of gamma-glutamyl amino acids leads to glutathionuria (see Anderson, M. E. et al, *Fed. Proc.* 41:5246 (1982), Meister, A. et al, *Ann. Rev. Biochem.* 52:711–760 (1983) and Anderson, M. E. et al, *Proc. Natl. Acad. Sci.*, USA, 80:707–711 (1983)).

The present invention was developed in order to overcome the above-described disadvantages of known inhibitors of gamma-glutamyl transpeptidase in combatting renal toxicity and is based in part on the finding that in the present invention gamma-glutamyl amino acids are non-toxic and specific inhibitors of gamma-glutamyl transpeptidase and are useful for combatting renal toxicity due to metals or nephrotoxic drugs.

It is known that leukotrienes of the C and E type (type C being the initial glutathione conjugate normally found) are converted by gamma-glutamyl transpeptidase to leukotrienes of the D and F type, respectively (see Hammarstrom, S., *Ann. Rev. Biochem.* 52:355–377 (1983)). The C, D, E and F types of leukotrienes have different physiological effects, e.g., these leukotrienes can produce different allergic responses. Some are more active than others depending upon the type of system being studied. As a result, it is advantageous to increase formation of one type as compared to another. It has been found in the present invention that gamma-glutamyl amino acids are useful for this purpose.

SUMMARY OF THE INVENTION

An object of the present invention is to provide a non-toxic and specific method for combatting renal toxicity due to metals.

Another object of the present invention is to provide a non-toxic and specific method for combatting renal toxicity due to nephrotoxic drugs.

Still another object of the present invention is to provide a method for selectively modulating in vivo formation of leukotriene types.

Other objects of the present invention can be discerned from the detailed description of the present invention hereinafter.

In one embodiment of the present invention, the above-described objects have been met by a method for combatting renal toxicity due to metals or nephrotoxic drugs comprising administering to a subject, a pharmaceutically acceptable amount of a gamma-glutamyl amino acid or a mixture of gamma-glutamyl amino acids.

In another embodiment of the present invention, the above-described objects have been met by a method for selectively modulating in vivo formation of leukotriene types comprising administering to a subject, a pharmaceutically acceptable amount of a gamma-glutamyl amino acid or a mixture of gamma-glutamyl amino acids.

BRIEF DESCRIPTION OF THE DRAWINGS

The FIGURE illustrates the correlation between urinary glutathione excretion and the apparent $K_{hi}$ values of gamma-glutamyl amino acids for gamma-glutamyl transpeptidase. Points (left to right) indicate <58 $\mu$M: gamma-glu-val, gamma-glu-asp, gamma-glu-$\epsilon$-lys, gamma-glu-ile, gamma-glu-leu, gamma-glu-gamma-glu-ala (in square). Other points (left to right) indicate: D-gamma-glu-met, gamma-glu-glu, gamma-glu-$\alpha$-amino butyrate (gama-glu-Aba), gamma-glu-(cys)$_2$, gamma-glu-gly, gamma-glu-tyr, gamma-glu-gly-gly, S-Me-glutathione, gamma-glu-glu, gamma-glu-ala, (gamma-glu-cys)$_2$, gamma-glu-met.

DETAILED DESCRIPTION OF THE INVENTION

As discussed above, in one embodiment of the present invention, the above-described objects have been met by a method for combatting renal toxicity due to metals, nephrotoxic drugs or both, comprising administering to a subject, a pharmaceutically acceptable amount of a gamma-glutamyl amino acid or a mixture of gamma-glutamyl amino acids.

Examples of the metals which form glutathione conjugates in vivo and thus give rise to renal toxicity for which the present invention is applicable include mercury, cadmum, lead, copper and selenium. Mercury, cadmium and lead are the clinically most toxic metals.

Examples of the nephrotoxic drugs which give rise to renal toxicity for which the present invention is applicable include gentamicin, streptomycin, cyclosporin and cis-platinum. Gentamycin, cyclosporin and cis-platinum are the clinically most nephrotoxic drugs.

Also, as discussed above, in another embodiment of the present invention, the above-described objects have been met by a method of selectively modulating in vivo formation of leukotriene types comprising administering to a subject a pharmaceutically acceptable amount of a gamma-glutamyl amino acid or a mixture of gamma-glutamyl amino acids.

It has been found in the present invention that gamma-glutamyl amino acids can be used to prevent conversion of type C leukotriene to type D leukotriene or prevent conversion of type E leukotriene to type F leukotriene, thereby selectively modulating formation of one type of leukotriene over another.

The specific gamma-glutamyl amino acid employed in the present invention are not critical. Examples of such gamma-glutamyl amino acids include (L-gamma-Glu-L-Cys)$_2$, L-Gamma-Glu-L-(Cys)$_2$, L-Gamma-Glu-L-Met, L-Gamma-Glu-L-Glu, L-Gamma-Glu-L-Ala, L-Gamma-Glu-L-Gamma-Glu-L-Ala, L-Gamma-Glu-Gly-Gly, L-Gamma-Glu-L-Tyr, L-Gamma-Glu-Gly, L-Gamma-Glu-L-Leu, L-Gamma-Glu-L-$\alpha$-Aba, L-Gamma-Glu-L-Gln, L-Gamma-Glu-L-Ile, L-Gamma-Glu-$\epsilon$-L-Lys, L-Gamma-Glu-L-Asp, L-Gamma-Glu-L-Val and D-Gamma-Glu-L-Met. The preferred gamma-glutamyl amino acids employed in the present invention include L-Gamma-Glu-L-Glu, L-Gamma-Glu-L-Ala, L-Gamma-Glu-L-Gamma-Glu-L-Ala, L-Gamma-Glu-Gly-Gly, L-Gamma-Glu-L-Tyr and L-Gamma-Glu-Gly. L-gamma-glutamyl amino acids are preferable to D-gamma glutamyl amino acids. If desired, mixtures of gamma-glutamyl acids can be employed so as to avoid production of amino acid imbalance.

The gamma-glutamyl amino acids of the present invention can be administered in a pharmaceutically effective amount so as to combat renal toxicity due to metals or nephrotoxic drugs or to selectively modulate in vivo formation of leukotriene types. The pharmaceutically acceptable amount to be administered will vary depending upon the age, weight and sex of the subject. However, in general, a suitable dosage which can be administered is 0.5 to 10 mM/Kg body weight. A preferred dosage to be administered is 4.0 to 6.0 mM/Kg body weight.

The following example is illustrative of the present invention and is in no way intended to limit the scope of the present invention.

EXAMPLE

Male Swiss Webster mice (20–27 g) were obtained from Taconic Farms (Germantown, N.Y.) and Hilltop Lab Animals (Scottsdale, Pa.).

Gamma-glutamyl amino acids were prepared by well known means (see Anderson, M. E. et al, *Methods Enzymol.* 113:555–564 (1986)) or were obtained from Vega Biochemicals (Tucson, Ariz.) and Sigma Chemical Co. (St. Lous, Mo.). The purity of the gamma-glutamyl amino acids were checked by chromatography on a Durrum Model 500 amino acid anaylzer.

Highly purified rate kidney gamma-glutamyl transpeptidase was prepared by well known means (see Tate, S. S. et al, *Methods Enzymol.* 113:400–419 (1986)). Bovine and porcine gamma-glutamyl transpeptidase can be obtained from Sigma Chemical Co. (St. Louis, Mo.).

The mice were fed ad libitum. Their urinary bladders were emptied by gentle abdominal pressure prior to subcutaneous injection of the gamma-glutamyl amino acids and urine was collected at 15 minute intervals for 1 hour in a tube containing 5 $\mu$l of 50% (w/v) 5-sulfosalicyclic acid. Elevated plasma glutathione levels were occasionally found after moderate abdominal pressure was applied to mice. For this reason, studies of urinary and plasma glutathione levels were carried out on different groups of mice.

Plasma, kidneys and livers were obtained and processed by well known means (see Anderson, M. E. et al, *J. Biol. Chem.* 255:9530–9533 (1980) and Anderson, M. E. et al, *Methods Enzymol.* 113:548–555 (1986)) and the concentration of glutathione therein was determined by the GSSG reductase-DTNB recycling assay (see Anderson, M. E. et al, *Methods Enzymol.* 113:548–555 (1986), Tietze, F., *Analytical Biochem.* 27:502–522 (1969) and Owens, C. et al, *Biochem. J.* 94:705–711 (1965)).

The urine samples were treated with 5mM dithiothreitol (pH 7.0) for 1 hour followed by derivatization with 2-vinylpyridine (see Griffith, O. W., *Analytical Biochem.* 106:207–212 (1980)). The derivatized samples were chromatographed on the amino acid analyzer using lithium citrate buffers (see Benson, J. V. et al, *Anal. Biochem.* 18:228–240 (1967)). The elution times for the vinylpyridine derivatives of gamma-glutamyl glutathione, gamma-glutamylcysteine, glutathione, cysteinylglycine and cysteine were 120, 163, 165, 220 and 235 minutes, respectively.

The results obtained are shown in the Table below.

of glutathione was about 6 mM. Using a similar protocol (see Griffith, O. W., *Proc. Natl. Acad. Sci.*, USA, 76:268–272 (1979)), 3.6–5.6 mM glutathione was found in the urine of mice injected with L-gamma-glutamyl-(o-carboxy)phenylhydrazide. Administration of the hydrazide led to about a 30% decrease in kidney glutathione levels and to about a 13% decrease in liver glutathione levels. On the other hand, administration of gamma-glutamylcysteine (or of related compounds) increases kidney glutathione levels (see Anderson, M. E., *Proc. Natl. Acad. Sci.*, USA, 80:707–711 (1983)) and does not affect liver glutathione levels. It has been shown that these compounds are effectively transported into the kidney and used directly by glutathione synthetase for glutathione synthesis leading to elevated levels of glutathione (see Anderson, M. E., *Proc. Natl. Acad. Sci.*, USA, 80:707–711 (1983)). In contrast, during the experimental period, i.e., 1 hour, it has been found that administration of other gamma-glutamyl amino acids does not significantly affect the glutathione levels of the kidney or liver. The levels of glutathione found in the blood plasma after the gamma-glutamyl amino acid administration varied in different experiments from the normal

TABLE

Induction of Glutathionuria by Gamma-Glutamyl Compounds*

| Exp. No. | Treatment | Urinary GSH, mM | No. of Mice |
|---|---|---|---|
| 1 | Saline (controls) | <0.01 | >20 |
| 2 | (L-Gamma-Glu—L-Cys)$_2$ | 5.77 ± 1.05 | 5 |
| 3 | L-Gamma-Glu—L-(Cys)$_2$ | 2.63 ± 0.33 | 4 |
| 4 | L-Gamma-Glu—L-Met | 8.54 ± 0.99 | 4 |
| 5 | L-Gamma-Glu—L-Glu | 5.28 ± 1.05 | 4 |
| 6 | L-Gamma-Glu—L-Ala | 5.69 ± 1.26 | 3 |
| 7 | L-Gamma-Glu—L-Gamma-Glu—L-Ala | 5.07 ± 0.73 | 3 |
| 7A | S—Methyl glutathione | 5.21 ± 1.30 | 4 |
| 8 | L-Gamma-Glu—Gly—Gly | 3.29 ± 1.16 | 8 |
| 9 | L-Gamma-Glu—L-Tyr | 3.19 ± 0.80 | 4 |
| 10 | L-Gamma-Glu—Gly | 2.67 ± 0.40 | 3 |
| 11 | L-Gamma-Glu—L-Leu | 0.60 ± 0.07 | 4 |
| 12 | L-Gamma-Glu—L-α-Aba | 1.52 ± 0.38 | 3 |
| 13 | L-Gamma-Glu—L-Gln | 1.17 ± 0.55 | 9 |
| 14 | L-Gamma-Glu—L-Ile | 1.00 ± 0.10 | 4 |
| 15 | L-Gamma—ε-L-Lys | 0.77 ± 0.17 | 3 |
| 16 | L-Gamma-Glu—L-Asp | 0.26 ± 0.10 | 4 |
| 17 | L-Gamma-Glu—L-Val | 0.49 ± 0.25 | 3 |
| 18 | D-Gamma-Glu—L-Met | 0.18 ± 0.05 | 10 |
| 19 | L-Cystine, L-(and D-)glutamine, L-glutamate plus L-cysteine, L-glutamate plus L-α-aminobutyrate, L-glu-L-tyr, L-glu-L-val, L-glu-L-(α)-lys, L-glu-L-ala | <0.03 | 3–4 (each) |

*The mice were injected subcutaneously with a 200 mM neutral solution of the indicated amino acid (dose, 4 mM per kilogram of body weight) or with an equivalent volume of saline. Urine was collected for 1 hour.

As indicated in the above Table, administration of the gamma-glutamyl derivatives of methionine, glutamate, alanine, gamma-glutamyl alanine, glycyl glycine, tyrosine, glycine and leucine was followed by substantial urinary excretion of glutathione. The amounts of glutathione excreted is estimated to be in the range of 3–6 mM, which is a significant fraction, perhaps 50–80%, of the total kidney tubular burden of glutathione. It is estimated that the amount of glutathione excreted during the experimental period can be as high as 5–8% of total body glutathione. Other gamma-glutamyl amino acids have also been found in the present invention to induce glutathionuria, whereas several α-glutamyl amino acids, free amino acids and mixtures of glutamate and cysteine (or α-aminobutyrate) do not.

Also, as seen from the Table, normal amounts of urine contains less than 0.01 mM glutathione (GSH). One hour after administration of gamma-glutamylcysteine disulfide (4 mM per Kg body weight) the urinary level range (20–40 μM) to about twice these values. These findings greatly differ from those found with the hydrazide and other inhibitors of gamma-glutamyl transpeptidase which lead to marked increases in plasma glutathione levels (see Griffith, O. W. et al, *Proc. Natl. Acad. Sci.*, USA, 76:268–272 (1979)).

It had been known that the administration of hydrazide inhibitors of gamma-glutamyl transpeptidase or AT-125 also induced urinary excretion of gamma-glutamyl cyst(e)ine (see Griffith, O. W. et al, *Proc. Natl. Acad. Sci.*, USA, 76:268–272 (1979) and Griffith, O. W. et al, *Proc. Natl. Acad. Sci.*, USA 77:3384–3387 (1980)). In the present invention the existence of gamma-glutamyl cysteine (as the vinylpyridine derivative) in the urine of mice that had been given gamma-glutamyl amino acids has also been observed. That is, when gamma-glutamyl glycyl glycine was given, the urine contained gamma-glutamyl cysteine at levels that were about 10% of those of glutathione. In addition, in these experiments and in studies in which gamma-glutamyl alanine was given, the urine also contained significant amounts of gamma-glutamyl glutathione (see Abbott, W. A., Proc. Natl. Acad. Sci., USA, 83:1246–1250 (1986) and of compounds that chromatographed in the elution positions of several gamma-glutamyl amino acids, but which were different from the administered gamma-glutamyl amino acid.

Analyses before and after reduction with dithiothreitol have shown that a considerable amount of urinary glutathione was in the form of a mixed disulfide, especially that between glutathione and cysteine, which is not a substrate of GSSG reductase. This indicates that the total excretion of glutathione moieties is probably much greater, perhaps by as much as 100%, than indicated by the data obtained by the GSSG-DTNB recycling assay shown in the Table.

Gamma-glutamyl transpeptidase activity was assayed using L-gamma-glutamyl-p-nitroanilide and the rate of formation of p-nitroaniline at 405 nm at 37° C. was measured (see Orlowski, M. et al, Biochim. Biophys. Acta 73:679–681 (1973)). The 1 ml final volume enzyme reaction mixture employed contained 40 mM Tris-HCl (pH 7.5), 30 or 60 $\mu$M L-gamma-glutamyl-p-nitroanilide, 30 or 150 $\mu$M gamma-glutamyl amino acid and 0.115 units gamma-glutamyl transpeptidase. Two different concentrations of substrate were employed for kinetic analyses. The reaction was initiated by adding gamma-glutamyl transpeptidase. The absorbance scale was 0.02 or 0.05 to insure that initial rates were obtained. The apparent hydrolysis Ki (Khi) values were determined from a Dixon plot and normalized to the apparent Km value for 6 $\mu$M L-gamma-glutamyl-p-nitroanilide (see Thompson, G. A. et al, Biochem. Biophys, Res. Commun. 71:32–36 (1976)).

The values for the apparent Khi for a number of gamma-glutamyl amino acids using purified rat kidney gamma-glutamyl transpeptidase are shown in the Figure. These values were plotted against the urinary glutathione obtained in the in vivo studies and a fairly close correlation was found. That is, the apparent affinity of gamma-glutamyl transpeptidase or gamma-glutamyl amino acid substrates varies over about a 6-fold range. In contrast, the affinity for the corresponding free amino acids varies over a range of several hundred (see Tate, S. S. et al, J. Biol. Chem. 249:7593–7602 (1974)). This demonstrated that the gamma-glutamyl moiety contributes significantly to binding. For example, such amino acids as aspartate, lysine and valine are extremely poor acceptor substrates whereas the corresponding gamma-glutamyl amino acids exhibit significant interaction with gamma-glutamyl transpeptidase. The data also demonstrates that glutamine, a very poor gamma-glutamyl substrate of the gamma-glutamyl transpeptidase, is ineffective in inducing glutathionuria. Gamma-glutamyl-gamma-glutamyl alanine, which induced glutathionuria (see the Figure) is rapidly converted in vivo to gamma-glutamyl alanine, which has a much higher affinity for gamma-glutamyl transpeptidase.

The amounts of glutathione found in the urine in the above studies reflects very substantial output of glutathione by renal cells and strongly supports the view that the kidney functions in a quantitatively significant cycles of glutathione transport and metabolism. Renal tubular glutathione is effectively utilized by gamma-glutamyl transpeptidase and dipeptidase and glutathione is also effective in metabolized basolaterally (see Abbott, W. A., J. Biol. Chem. 259:15,393–15,400 (1984)). Thus, the substantial output of glutathione by the kidney plus glutathione derived from the blood plasma is matched by efficient utilization of glutathione in the tubule and in the basolateral circulation so that very little glutathione reaches the urine and the renal venous plasma.

Although gamma-glutamylcysteine and closely related compounds increase kidney levels of glutathione (see Anderson, M. E. et al, Proc. Natl. Acad. Sci., USA, 80:707–711 (1983)), the gama-glutamyl derivatives of the other amino acids studied did not effect kidney glutathione levels significantly during the experimental period. No affect of gamma-glutamyl amino acids on liver glutathione levels has been found nor was any toxicity apparent. Administration of gamma-glutamyl amino acids also inhibits gamma-glutamyl transpeptidase in other tissues but does not produce other serious perturbation of metabolism. This is consistent with the findings of elevated plasma glutathione levels in some experiments.

While this invention has been described in detail and with reference to specific embodiments thereof, it will be apparent to one skilled in the art that various changes and modifications could be made therein without departing from the spirit and scope thereof.

We claim:

1. A method for combatting renal toxicity due to metals, nephrotoxic drugs or both, comprising administering to a subject, a pharmaceutically acceptable amount of a gamma-glutamyl amino acid or a mixture of gamma-glutamyl amino acids.

2. The method as claimed in claim 1, wherein said metal is selected from the group consisting of mercury, cadmium, lead and copper and said nephrotoxic drug is selected from the group consisting of gentamicin, streptomycin, cyclosporin and cis-platinum.

3. The method as claimed in claim 1, wherein said gamma-glutamyl amino acid is selected from the group consisting of (L-gamma-Glu-L-Cys)$_2$, L-Gamma-Glu-L-(Cys)$_2$, L-Gamma-Glu-L-Met, L-Gamma-Glu-L-Glu, L-Gamma-Glu-L-Ala, L-Gamma-Glu-L-Gamma-Glu-L-Ala, L-Gamma-Glu-Gly-Gly, L-Gamma-Glu-L-Tyr, L-Gamma-Glu-Gly, L-Gamma-Glu-L-Leu, L-Gamma-Glu-L-$\alpha$-Aba, L-Gamma-Glu-L-Gln, L-Gamma-Glu-L-Ile, L-Gamma-Glu-$\epsilon$-L-Lys, L-Gamma-Glu-L-Asp, L-Gamma-Glu-L-Val and D-Gamma-Glu-L-Met.

4. The method as claimed in claim 3, wherein said gamma-glutamyl amino acid is selected from the group consisting of L-Gamma-Glu-L-Glu, L-Gamma-Glu-L-Ala, L-Gamma-Glu-L-Gamma-Glu-L-Ala, L-Gamma-Glu-Gly-Gly, L-Gamma-Glu-L-Tyr and L-Gamma-Glu-Gly.

5. The method as claimed in claim 1, wherein said pharmaceutically acceptable amount is 0.5 to 10 mM/Kg body weight.

6. The method as claimed in claim 5, wherein said pharmaceutically acceptable amount is 4.0 to 6.0 mM/Kg body weight.

* * * * *